(12) United States Patent
Huang et al.

(10) Patent No.: US 12,733,800 B2
(45) Date of Patent: Sep. 15, 2026

(54) CAPSULE ENDOSCOPE, ENDOSCOPE SYSTEM AND IMAGE CORRECTION METHOD

(71) Applicant: Pro-Sight Medical Technology CORP., LTD., Miaoli County (TW)

(72) Inventors: Sheng Wen Huang, Miaoli County (TW); Ai-Ke Huang, Hsinchu City (TW); Jr-Je Chuang, Changhua County (TW); Hsiao-Chun Hsu, Taichung City (TW); Ya-Hsuan Lee, Hsinchu City (TW)

(73) Assignee: Pro-Sight Medical Technology CORP., LTD., Miaoli County (TW)

( * ) Notice: Subject to any disclaimer, the term of this patent is extended or adjusted under 35 U.S.C. 154(b) by 547 days.

(21) Appl. No.: 18/352,212

(22) Filed: Jul. 13, 2023

(65) Prior Publication Data

US 2024/0016373 A1 Jan. 18, 2024

(30) Foreign Application Priority Data

Jul. 18, 2022 (TW) ................................ 111126844

(51) Int. Cl.
*A61B 1/04* (2006.01)
*A61B 1/00* (2006.01)

(52) U.S. Cl.
CPC ........ *A61B 1/041* (2013.01); *A61B 1/000095* (2022.02); *A61B 1/00045* (2013.01)

(58) Field of Classification Search
CPC .............. A61B 1/041; A61B 1/000095; A61B 1/00045; A61B 1/00006; A61B 1/00009
See application file for complete search history.

(56) References Cited

U.S. PATENT DOCUMENTS

| | | | | |
|---|---|---|---|---|
| 2002/0161280 | A1* | 10/2002 | Chatenever | A61B 1/042 600/137 |
| 2011/0249952 | A1* | 10/2011 | Taniguchi | G16H 30/20 386/E5.028 |
| 2012/0157769 | A1* | 6/2012 | Zhu | A61B 1/0002 600/109 |
| 2013/0038711 | A1* | 2/2013 | Sato | A61B 1/00158 348/E7.085 |
| 2015/0138329 | A1 | 5/2015 | Braun et al. | |

FOREIGN PATENT DOCUMENTS

| | | |
|---|---|---|
| CN | 101652092 | 2/2010 |
| CN | 202283246 | 6/2012 |
| CN | 103876703 | 6/2014 |
| CN | 114066781 | 2/2022 |
| TW | 201347720 | 12/2013 |
| TW | 201532589 | 9/2015 |

* cited by examiner

*Primary Examiner* — Michael J Carey
*Assistant Examiner* — William B Chou
(74) *Attorney, Agent, or Firm* — JCIPRNET

(57) ABSTRACT

A capsule endoscope, an endoscope system, and an image correction method are provided. The capsule endoscope includes an image sensor and a posture sensor. The image sensor is coupled to a processor and obtains a sensed image. The posture sensor is coupled to the processor and obtains three-axis data. The processor calculates a screen rotation angle according to the three-axis data and corrects the sensed image according to the screen rotation angle. A first axis and a second axis of the corrected sensed image rotate toward an actual vertical axis and an actual horizontal axis.

12 Claims, 6 Drawing Sheets

CAPSULE ENDOSCOPE, ENDOSCOPE SYSTEM AND IMAGE CORRECTION METHOD

CROSS-REFERENCE TO RELATED APPLICATION

This application claims the priority benefit of Taiwan application serial no. 111126844, filed on Jul. 18, 2022. The entirety of the above-mentioned patent application is hereby incorporated by reference herein and made a part of this specification.

BACKGROUND

Technical Field

The disclosure relates to an endoscope, and in particular relates to a capsule endoscope, an endoscope system, and an image correction method.

Description of Related Art

The problem often encountered in the use of the existing capsule endoscope is that when the capsule endoscope is placed in the body of a subject to be diagnosed, the operator cannot effectively grasp the posture of the capsule endoscope in the body of the subject to be diagnosed. Moreover, since the posture of the capsule endoscope in the body of the subject to be diagnosed may rotate arbitrarily, the image provided by the capsule endoscope may also rotate arbitrarily, which may cause the subject to be diagnosed to be uncomfortable or cause the image on the screen watched by the operator to be difficult to identify, or even a misjudgment of the content of the image may happen.

SUMMARY

The disclosure provides a capsule endoscope, an endoscope system, and an image correction method, which can automatically correct an image horizontal, so that a proper sensed image can be presented.

The capsule endoscope of the disclosure includes an image sensor and a posture sensor. The image sensor is coupled to a processor and obtains a sensed image. The posture sensor is coupled to the processor and obtains three-axis data. The processor calculates a screen rotation angle according to the three-axis data and corrects the sensed image according to the screen rotation angle. A first axis and a second axis of the corrected sensed image rotate toward an actual vertical axis and an actual horizontal axis.

The endoscope system of the disclosure includes a computer device and a capsule endoscope. The computer device includes a display device. The capsule endoscope is coupled to the computer device. The capsule endoscope includes an image sensor and a posture sensor. The image sensor is coupled to a processor and obtains a sensed image. The posture sensor is coupled to the processor and obtains three-axis data. The processor calculates a screen rotation angle according to the three-axis data and corrects the sensed image according to the screen rotation angle. A first axis and a second axis of the corrected sensed image rotate toward an actual vertical axis and an actual horizontal axis of the posture sensor. The processor outputs the corrected sensed image to the display device of the computer device, so that the display device displays the corrected sensed image.

An image correction method of the disclosure is suitable for a capsule endoscope. The capsule endoscope includes an image sensor and a posture sensor. The image correction method includes the following. A sensed image is obtained through the image sensor. Three-axis data is obtained through the posture sensor. A screen rotation angle is calculated according to the three-axis data. The sensed image is corrected according to the screen rotation angle, in which a first axis and a second axis of the corrected sensed image rotate toward an actual vertical axis and an actual horizontal axis of the posture sensor.

Based on the above, the capsule endoscope, the endoscope system, and the image correction method of the disclosure can sense current three-axis data of the capsule endoscope in real time through the posture sensor, so that the sensed image can be automatically corrected according to the current three-axis data of the capsule endoscope, so that the display device of the computer device can present a proper sensed image.

In order to make the above-mentioned features and advantages of the disclosure more comprehensible, the following embodiments are described in detail together with the accompanying drawings.

DESCRIPTION OF THE EMBODIMENTS

Figure 1:
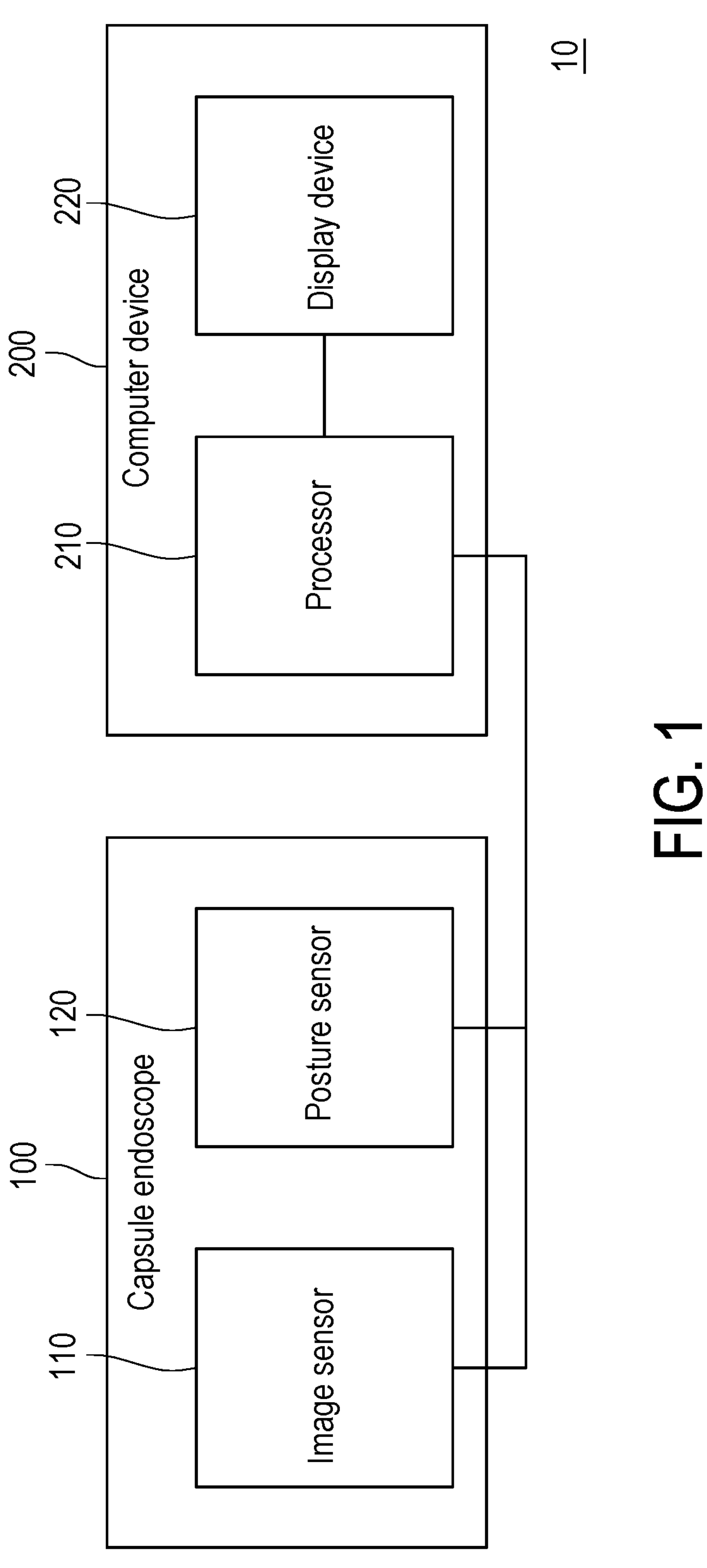
FIG. 1 is a schematic circuit diagram of an endoscope system according to an embodiment of the disclosure.

In order to make the content of the disclosure more comprehensible, the following embodiments are given as examples in which the disclosure may indeed be implemented. In addition, wherever possible, elements/members/steps with the same reference numerals are used in the drawings and embodiments to represent the same or similar components.

FIG. 1 is a schematic circuit diagram of an endoscope system according to an embodiment of the disclosure. Referring to FIG. 1, an endoscope system 10 includes a capsule endoscope 100 and a computer device 200. In this embodiment, the capsule endoscope 100 includes an image sensor 110 and a posture sensor 120. The image sensor 110 may be, for example, a CMOS image sensor (CIS) or a sensor including a charge coupled device (CCD), and may also include a related optical lens mechanism. The posture sensor 120 may include at least one of a gyroscope sensor and an accelerometer sensor. In an embodiment, the posture sensor 120 may be a six-axis gyroscope (a three-axis gyroscope and a three-axis accelerometer sensor).

In this embodiment, the computer device 200 may be, for example, a personal computer, an industrial computer, a laptop computer, or a tablet computer. The computer device 200 includes a processor 210 and a display device 220. The processor 210 may be, for example, a graphics processing unit (GPU), an image processing unit (IPU), an image signal processor (ISP), a central processing unit (CPU), a field programmable gate array (FPGA), or other processing units with computing functions or combinations thereof.

In this embodiment, the capsule endoscope 100 is coupled to the computer device 200 via a physical connection line. The processor 210 is coupled to the display device 220 and is coupled to the image sensor 110 and the posture sensor 120 through physical connection lines. In other words, the capsule endoscope 100 in this embodiment is a capsule endoscope with lines. In this embodiment, the image sensor 110 and the posture sensor 120 may transmit a sensed image and three-axis data to the processor 210. In this embodiment, the processor 210 may be used to correct the sensed image provided by the image sensor 110 according to the three-axis data and provide a corrected sensed image to the display device 220, so that the display device 220 can display the corrected sensed image.

However, in an embodiment, the processor 210 may also be disposed in the capsule endoscope 100 and coupled to the image sensor 110 and the posture sensor 120. In this regard, the processor in the capsule endoscope 100 may be coupled to another processor of the computer device 200 through the physical connection line, so as to provide the corrected sensed image to the computer device 200 through the physical connection line. The processor 210 may be, for example, a microprocessor chip disposed in the capsule endoscope 100 and has an image processing function. In this embodiment, the microprocessor chip may transmit the sensed image and the three-axis data to the processor 210 according to the universal serial bus video device class (UVC) protocol. The image sensor 110 and the posture sensor 120 may convert image data and three-axis data of the sensed image into a data format of the UVC protocol through the microprocessor chip, so as to transmit the image data to the processor 210 through a data packet of the UVC protocol. In other words, the capsule endoscope 100 may also correct the image first and then output to the computer device 200, so that the computer device 200 can directly display the corrected sensed image through the display device 220.

In addition, the capsule endoscope 100 of this embodiment may also include other necessary components and modules, such as a control module, a lens module, a magnet, a light source module or wires, but the disclosure is not limited thereto. Moreover, the endoscope system 10 of this embodiment may also include, for example, a magnetic handle, which may be used to control the position and posture of the capsule endoscope 100 in a subject to be diagnosed.

Figure 2:
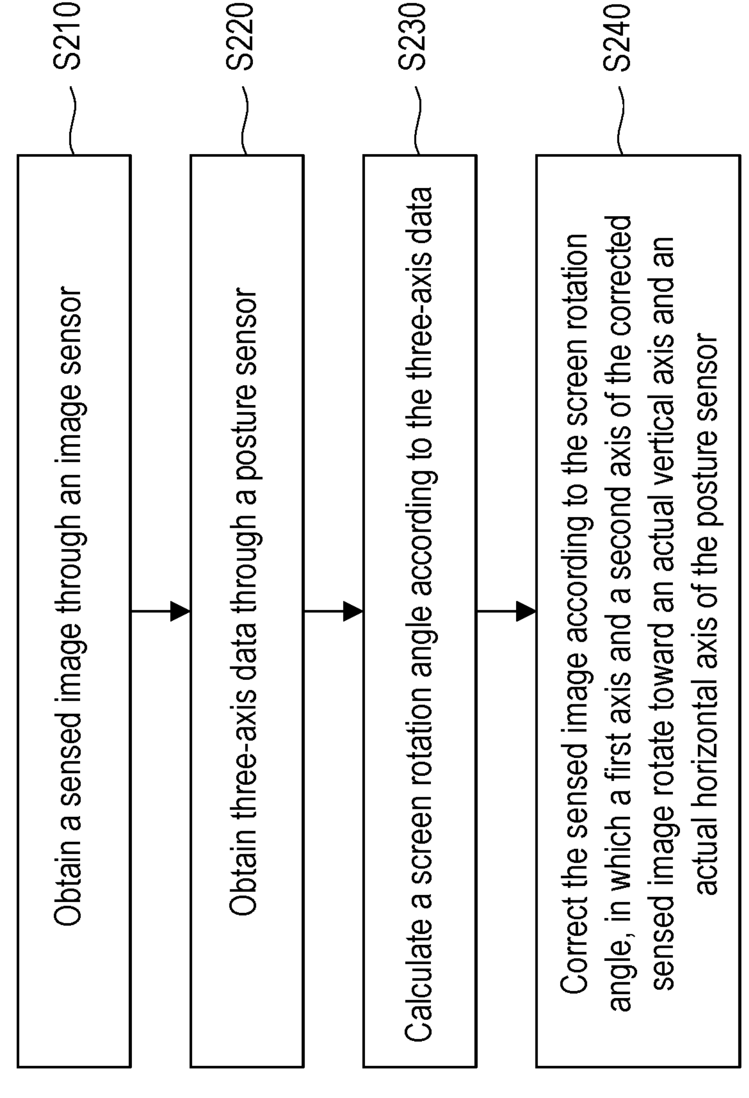
FIG. 2 is a flowchart of an image correction method according to an embodiment of the disclosure.

FIG. 2 is a flowchart of an image correction method according to an embodiment of the disclosure. Referring to FIG. 1 and FIG. 2, the endoscope system 10 may execute the image correction method as the following Steps S210 to S240. In this embodiment, when the operator places the capsule endoscope 100 into the body of the subject to be diagnosed, in Step S210, the endoscope system 10 may obtain a sensed image through the image sensor 110 of the capsule endoscope 100. In this embodiment, the image sensor 110 takes images continuously to generate dynamic images. In Step S220, the endoscope system 10 may obtain three-axis data through the posture sensor 120 of the capsule endoscope 100. In this embodiment, the three-axis data refers to current three-axis orientation information (such as an X-axis, a Y-axis, and a Z-axis) of the capsule endoscope 100. In Step S230, the endoscope system 10 may calculate a screen rotation angle according to the three-axis data through the processor 210. In Step S240, the endoscope system 10 may correct the sensed image according to the screen rotation angle through the processor 210. A first axis and a second axis of the corrected sensed image (that is, an X "axis and a Y" axis of the image sensor 110 described below) rotate toward an actual vertical axis (that is, the real gravity axis) and an actual horizontal axis (that is, the real horizontal axis perpendicular to the real gravity axis) provided by the posture sensor. In this regard, the correction method of the sensed image will be described in detail in the following embodiments. Therefore, the image correction method of this embodiment can automatically and dynamically correct the image horizontal of the sensed image to present a proper sensed image effect.

Figure 3:
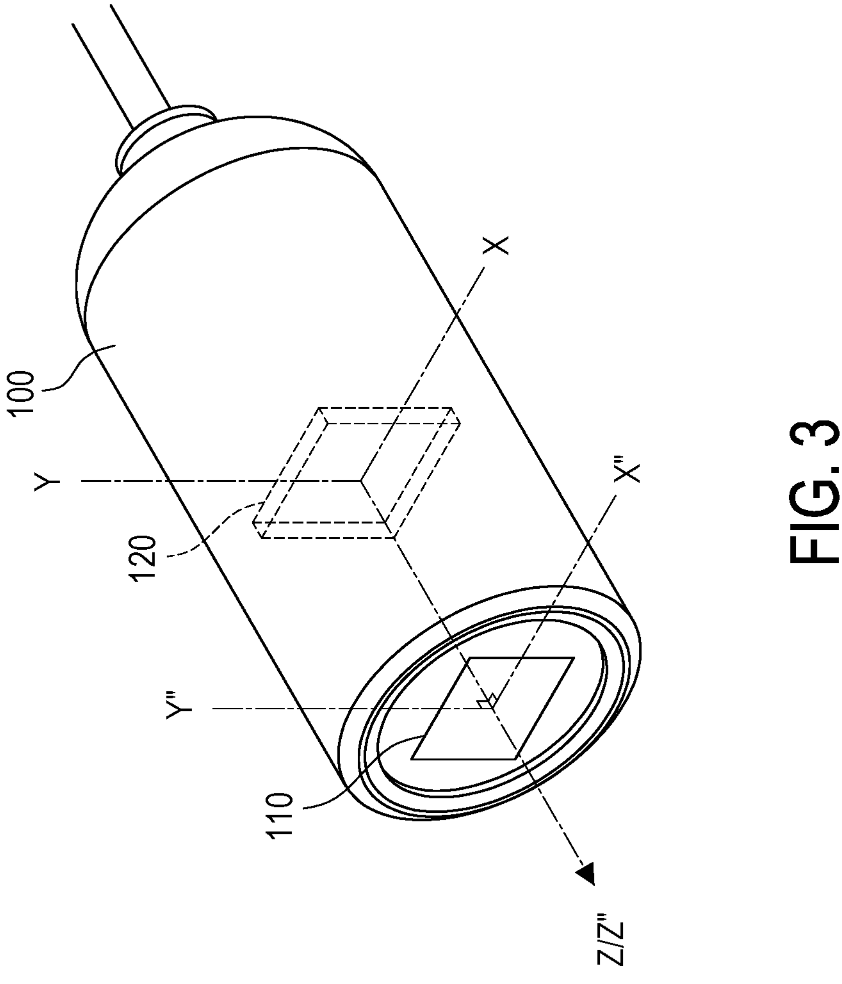
FIG. 3 is a schematic diagram of a capsule endoscope according to an embodiment of the disclosure.

FIG. 3 is a schematic diagram of a capsule endoscope according to an embodiment of the disclosure. Referring to FIG. 1 and FIG. 3, the capsule endoscope 100 of the disclosure may, for example, realize an aspect shown in FIG. 3. In this embodiment, the image sensor 110 of the capsule endoscope 100 may be disposed at a front end of the capsule endoscope 100 and may be disposed with a related optical lens. The posture sensor 120 of the capsule endoscope 100 may be disposed in a casing of the capsule endoscope 100 and symmetrically arranged with the image sensor 110. Therefore, the X axis and the Y axis of the posture sensor 120 are respectively parallel to the X" axis and the Y" axis of the image sensor 110, and the Z" axis of the image sensor 110 (that is, a sensing axis (sensing direction) of the image sensor 110) overlaps (or is parallel to) a Z axis of the posture sensor. In other words, the processor 210 may use the three-axis information provided by the posture sensor 120 to calculate or directly use as direction information of the first axis and the second axis (that is, equal to the X" axis and Y" axis of the image sensor 110) of the sensed image provided by the image sensor 110. In this way, when the capsule endoscope 100 rotates in the body of the subject to be diagnosed so that the X" axis and the Y" axis of the image sensor 110 are not parallel to the actual vertical axis and the actual horizontal axis, the processor 210 may calculate the screen rotation angle so as to effectively correct the image horizontal of the sensed image according to the three-axis data of the current X-axis, Y-axis, and Z-axis output by the posture sensor 120.

Figure 4:
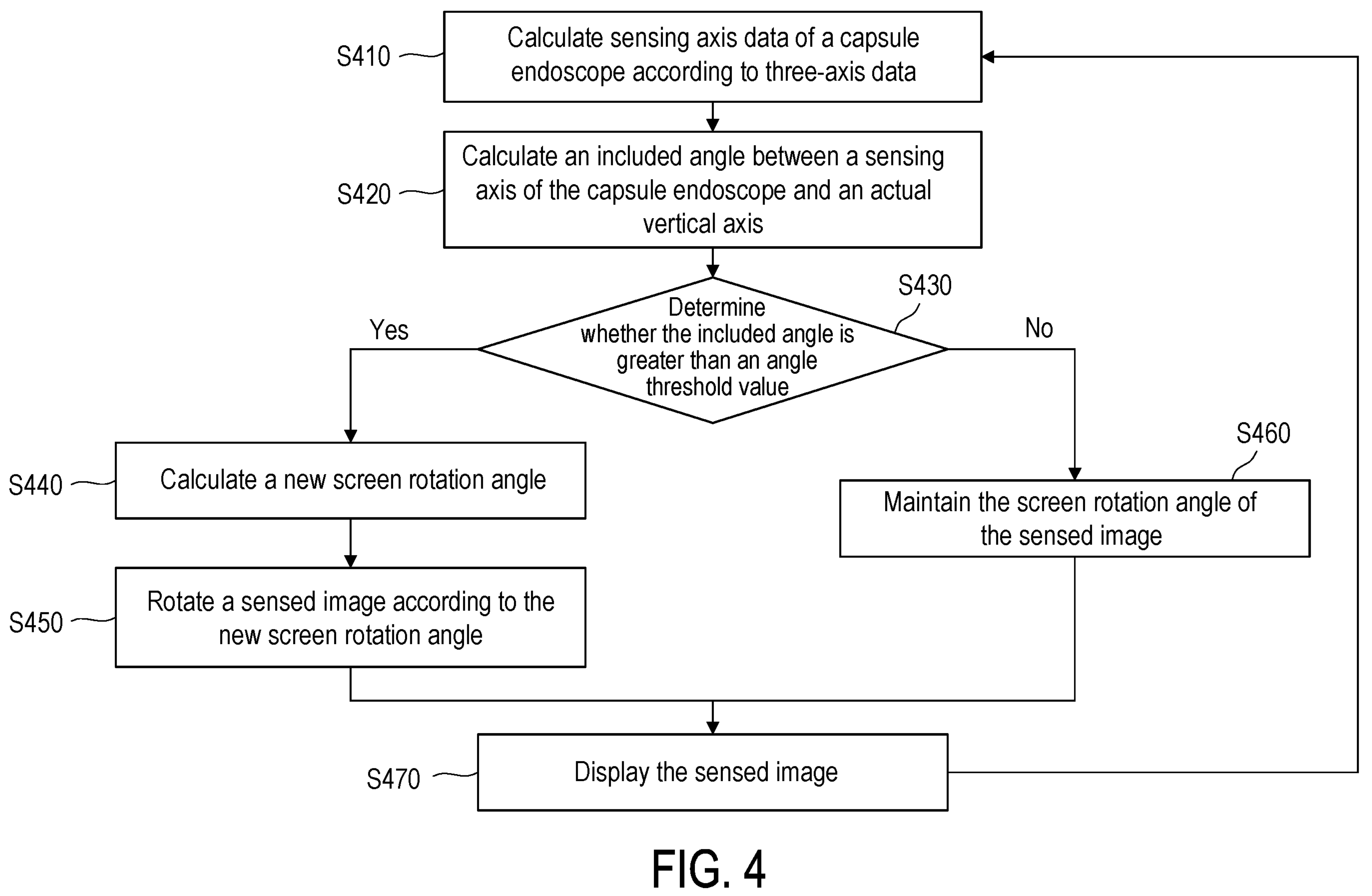
FIG. 4 is a flowchart of an image correction method according to another embodiment of the disclosure.
Figure 5:
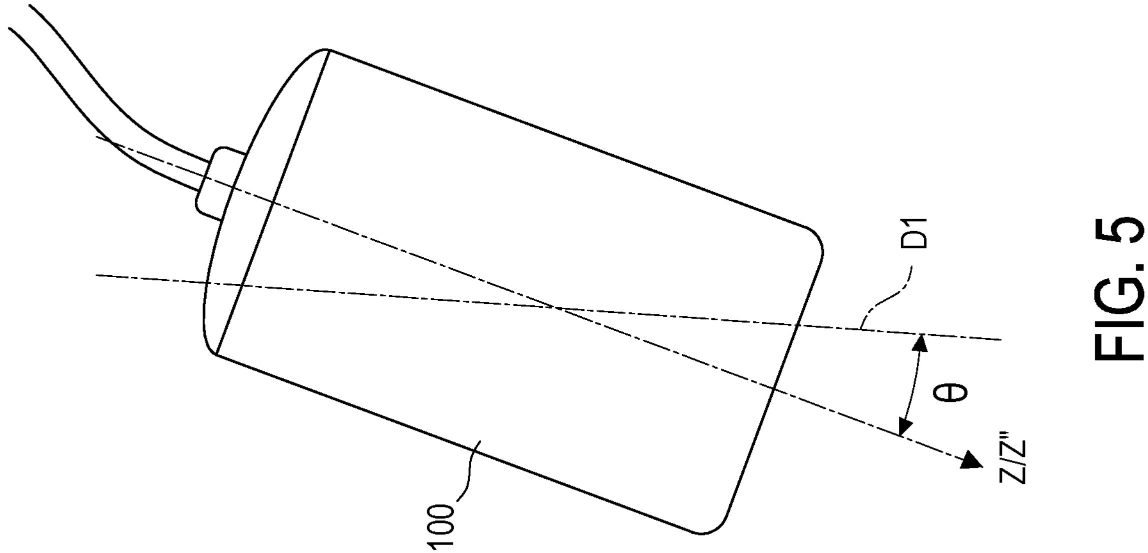
FIG. 5 is a schematic diagram of operating the capsule endoscope according to an embodiment of the disclosure.

FIG. 4 is a flowchart of an image correction method according to another embodiment of the disclosure. FIG. 5 is a schematic diagram of operating the capsule endoscope according to an embodiment of the disclosure. Referring to FIG. 1, FIG. 4, and FIG. 5, the endoscope system 10 may execute the image correction method as the following Steps S410 to S470. In this embodiment, when the operator places the capsule endoscope 100 into the body of the subject to be diagnosed, the processor 210 may execute the following Steps S410 to S470 for each frame or in each display cycle interval, so as to dynamically correct the image horizontal of the sensed image.

In Step S410, the processor 210 may calculate sensing axis data of the capsule endoscope 100 according to the three-axis data. In this embodiment, the sensing axis data may include, for example, three-axis direction data of the capsule endoscope 100 in a 3-dimensional space. In Step S420, the processor 210 may calculate an included angle θ between the sensing axis of the capsule endoscope 100 (i.e., the Z" axis of the image sensor 110 and the Z axis of the posture sensor) and an actual vertical axis D1 according to the sensing axis data. In Step S430, the processor 210 may determine whether the included angle θ is greater than an angle threshold value, in which the angle threshold value may be, for example, 5 degrees. If the included angle θ is greater than the angle threshold value, then in Step S440, the processor 210 may calculate a new screen rotation angle. In Step S450, the processor 210 may rotate the sensed image according to the new screen rotation angle. If the included angle θ is smaller than or equal to the angle threshold value, then in Step S460, the processor 210 may maintain the current screen rotation angle of the sensed image. In Step S470, the processor 210 may provide the corrected sensed image to the display device 220 of the computer device 200 to display the (corrected) sensed image, and execute Step S410 cyclically. In other words, the endoscope system 10 of this embodiment may determine that if the current sensing posture of the capsule endoscope 100 is looking down or looking up (the included angle θ is smaller than or equal to the angle threshold value), then there is no need to rotate the image to avoid misjudgment of images by the diagnostic personnel or discomfort to image viewers due to excessive rotation of the image.

Figure 6A:
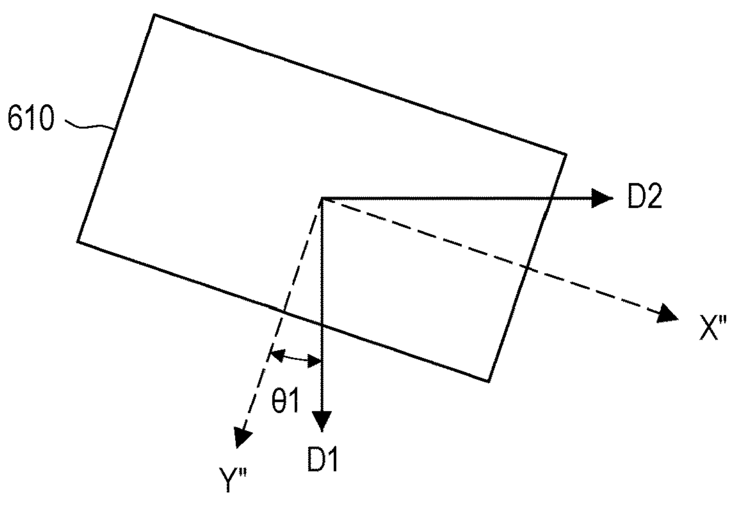
FIG. 6A to FIG. 6C are schematic diagrams of correcting a sensed image according to an embodiment of the disclosure.
Figure 6B:
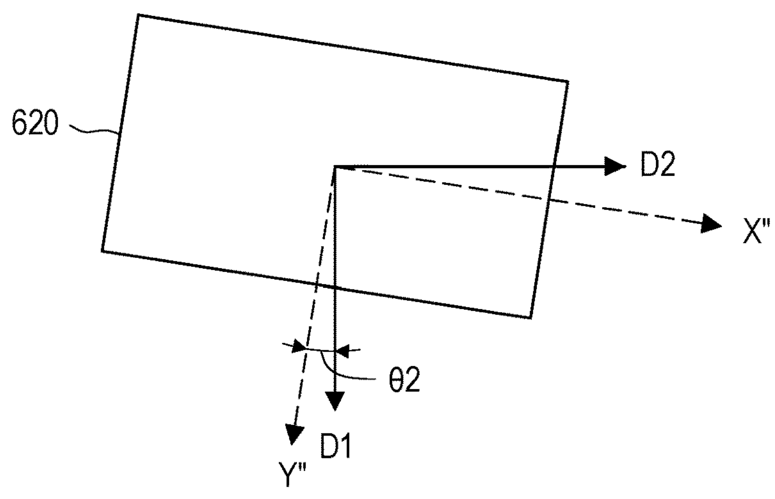
Figure 6C:
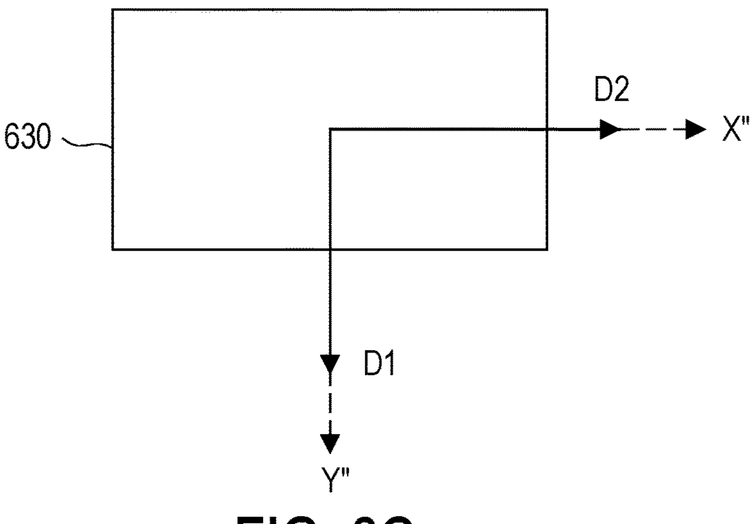

FIG. 6A to FIG. 6C are schematic diagrams of correcting a sensed image according to an embodiment of the disclosure. The following embodiment illustrates the manner in which the processor 210 in Step S440 above calculates the screen rotation angle. Referring first to FIG. 1 and FIG. 6A, in this embodiment, the processor 210 may obtain the X" axis and Y" (that is, equal to the first axis and the second axis of a sensed image 610) of the image sensor 110 according to the current three-axis data (that is, the X axis and the Y axis of the posture sensor 120) provided by the posture sensor 120 and calculate an included angle θ1 (equal to an included angle between an actual horizontal axis D2 and the Y" axis of the image sensor 110) between the actual vertical axis D1 provided by the posture sensor 120 and the X" axis of the image sensor 110. Next, the processor 210 may use the included angle θ1 as a target rotation angle and calculate the screen rotation angle by using, for example, a PID (proportional/differential/integral) controller algorithm. However, the method of calculating the screen rotation angle by the processor 210 of the disclosure is not limited thereto. In an embodiment, the processor 210 may also calculate and obtain the screen rotation angle through other types of controller algorithms. Therefore, the processor 210 may rotate the sensed image 610 according to the screen rotation angle.

Next, with reference to FIG. 6B, in the next frame or in the next display cycle interval, the sensed image 610 in FIG. 6A may be rotated to present a sensed image 620 as shown in FIG. 6B. In addition, the processor 210 may execute S410 to S470 cyclically to obtain the X" axis and the Y" axis (that is, the first axis and the second axis of the sensed image 610) of the image sensor 110 again according to current three-axis data (that is, the X axis and the Y axis of the posture sensor 120) provided by the posture sensor 120 and calculate an included angle θ2 (equal to an included angle between the actual horizontal axis D2 and the Y" axis of the image sensor 110) between the actual vertical axis D1 provided by the posture sensor 120 and the X" axis of the image sensor 110. Next, the processor 210 may use the included angle θ2 as a new target rotation angle and calculate a new screen rotation angle by using, for example, a PID (proportional/differential/integral) controller algorithm. Therefore, the processor 210 may rotate the sensed image 620 again according to the new screen rotation angle.

Next, with reference to FIG. 6C, after several frames or several display cycle intervals, the sensed image 620 in FIG. 6B may be rotated to present a sensed image 630 as shown in FIG. 6C, so that the X" axis and the Y" axis of the image sensor 110 are parallel to the actual vertical axis D1 and the actual horizontal axis D2 respectively. In other words, the first axis and the second axis of the sensed image displayed by the display device 220 gradually rotate toward the actual vertical axis and the actual horizontal axis provided by the posture sensor 120. Moreover, the display device 220 may display a continuous image presentation effect of gradually rotating the sensed image (the image gradually straightens). Alternatively, in an embodiment, the processor 210 also directly uses the included angle θ1 between the actual vertical axis D1 and the X" axis of the image sensor 110 of each calculation as the screen rotation angle, and in the next frame or in the next display cycle interval, the display device 220 can display the sensed image directly straightened.

In summary, the capsule endoscope, the endoscope system, and the image correction method of the disclosure can obtain the real-time three-axis data of the capsule endoscope through the posture sensor, so as to automatically and dynamically correct the image horizontal of the sensed image according to the real-time three-axis data to provide a proper endoscopic image for identification or diagnosis. Moreover, the capsule endoscope, the endoscope system, and the image correction method of the disclosure can also effectively avoid misjudgment of images by the diagnostic personnel or discomfort to image viewers due to excessive rotation of the image when the sensing posture of the capsule endoscope is looking down or looking up.

Although the disclosure has been disclosed above with the embodiments, the embodiments are not intended to limit the disclosure. Persons with ordinary knowledge in the technical field may make some changes and modifications without departing from the spirit and scope of the disclosure. The scope of protection of the disclosure should be defined by the scope of the appended claims.

What is claimed is:

1. A capsule endoscope comprising:

an image sensor coupled to a processor and obtaining a sensed image; and a posture sensor coupled to the processor and obtaining three-axis data, wherein the processor calculates a screen rotation angle according to the three-axis data and corrects the sensed image according to the screen rotation angle, wherein a first axis and a second axis of the corrected sensed image rotate toward an actual vertical axis and an actual horizontal axis, wherein a sensing axis of the image sensor is equal to a Z axis of the posture sensor, wherein the processor calculates sensing axis data of the capsule endoscope according to the three-axis data, and the processor determines whether an included angle between a sensing axis of the capsule endoscope and the actual vertical axis is greater than an angle threshold value to determine whether to correct the sensed image, wherein the angle threshold value is a not-zero angle threshold value, wherein when the processor determines that the included angle between the sensing axis and the actual vertical axis is smaller than or equal to the angle threshold value, the processor maintains the screen rotation angle of the sensed image, wherein when the processor determines that the included angle between the sensing axis and the actual vertical axis is greater than the angle threshold value, the processor calculates a new screen rotation angle and rotates the sensed image according to the new screen rotation angle.

2. The capsule endoscope as claimed in claim 1, wherein the capsule endoscope is coupled to a computer device via a physical connection line.

3. The capsule endoscope as claimed in claim 1, wherein the processor outputs the corrected sensed image to a display device of a computer device, so that the display device displays the corrected sensed image.

4. The capsule endoscope as claimed in claim 1, wherein the processor is disposed in a computer device or the capsule endoscope.

5. The capsule endoscope as claimed in claim 1, wherein the image sensor and the posture sensor transmit the sensed image and the three-axis data to the processor according to a universal serial bus video device class (UVC) protocol.

6. The capsule endoscope as claimed in claim 1, wherein the posture sensor comprises at least one of a gyroscope sensor and an accelerometer sensor.

7. An endoscope system comprising:

a computer device comprising a display device; and a capsule endoscope coupled to the computer device and comprising:

an image sensor coupled to a processor and obtaining a sensed image; and a posture sensor coupled to the processor and obtaining three-axis data, wherein the processor calculates a screen rotation angle according to the three-axis data and corrects the sensed image according to the screen rotation angle, wherein a first axis and a second axis of the corrected sensed image rotate toward an actual vertical axis and an actual horizontal axis of the posture sensor, wherein the processor outputs the corrected sensed image to a display device of the computer device, so that the display device displays the corrected sensed image, wherein a sensing axis of the image sensor is equal to a Z axis of the posture sensor, wherein the processor calculates sensing axis data of the capsule endoscope according to the three-axis data, and the processor determines whether an included angle between a sensing axis of the capsule endoscope and the actual vertical axis is greater than an angle threshold value to determine whether to correct the sensed image, wherein the angle threshold value is a not-zero angle threshold value, wherein when the processor determines that the included angle between the sensing axis and the actual vertical axis is smaller than or equal to the angle threshold value, the processor maintains the screen rotation angle of the sensed image, wherein when the processor determines that the included angle between the sensing axis and the actual vertical axis is greater than the angle threshold value, the processor calculates a new screen rotation angle and rotates the sensed image according to the new screen rotation angle.

8. The endoscope system as claimed in claim 7, wherein the capsule endoscope is coupled to the computer device via a physical connection line.

9. The endoscope system as claimed in claim 7, wherein the processor is disposed in the computer device or the capsule endoscope.

10. The endoscope system as claimed in claim 7, the image sensor and the posture sensor transmit the sensed image and the three-axis data to the processor according to a universal serial bus video device class (UVC) protocol.

11. The endoscope system as claimed in claim 7, wherein the posture sensor comprises at least one of a gyroscope sensor and an accelerometer sensor.

12. An image correction method, suitable for a capsule endoscope, wherein the capsule endoscope comprises an image sensor and a posture sensor, wherein the image correction method comprises:

obtaining a sensed image through the image sensor;

obtaining three-axis data through the posture sensor;

calculating a screen rotation angle according to the three-axis data; and correcting the sensed image according to the screen rotation angle, wherein a first axis and a second axis of the corrected sensed image rotate toward an actual vertical axis and an actual horizontal axis of the posture sensor, wherein correcting the sensed image comprises:

calculating sensing axis data of the capsule endoscope according to the three-axis data; and determining whether an included angle between a sensing axis of the capsule endoscope and an actual vertical axis is greater than an angle threshold value according to the sensing axis data to determine whether to correct the sensed image, wherein the angle threshold value is a not-zero angle threshold value, maintaining the screen rotation angle of the sensed image when the included angle between the sensing axis and the actual vertical axis is smaller than or equal to the angle threshold value; and calculating a new screen rotation angle and rotating the sensed image according to the new screen rotation angle when determining that the included angle between the sensing axis and the actual vertical axis is greater than the angle threshold value.

* * * * *